United States Patent [19]

Kitao et al.

[11] 4,367,019

[45] Jan. 4, 1983

[54] IMAGE ROTATING MEANS FOR EYE REFRACTOMETERS

[75] Inventors: Ikuo Kitao; Kiichi Kamiyama, both of Tokyo, Japan

[73] Assignee: Tokyo Kogaku Kikai Kabushiki Kaisha, Tokyo, Japan

[21] Appl. No.: 142,720

[22] Filed: Apr. 22, 1980

[30] Foreign Application Priority Data

Apr. 27, 1979 [JP] Japan ................................ 54-52241

[51] Int. Cl.³ .............................................. A61B 3/10
[52] U.S. Cl. .................................... 351/211; 351/214; 351/205
[58] Field of Search ................................ 351/13, 14, 6

[56] References Cited

U.S. PATENT DOCUMENTS 4,125,320  11/1978  Rassow et al. ........................ 351/13

Primary Examiner—Vincent P. McGraw
Assistant Examiner—Rodney B. Bovernick
Attorney, Agent, or Firm—Brumbaugh, Graves, Donohue & Raymond

[57] ABSTRACT

Eye refractometer including a target projecting optical system for projecting a target image on the retina of a patient's eye, and an observing optical system for observing the target image. An image rotator is provided for rotating the target image to thereby locate the astigmatic axes. The image rotator is associated with a rotating mechanism which includes an actuating member for producing a stepless rotation of the image rotator and a second member for rotating the first member by an angle corresponding to a 90° rotation of the target image.

3 Claims, 3 Drawing Figures

IMAGE ROTATING MEANS FOR EYE REFRACTOMETERS

The present invention relates to eye refractometers in which refractive powers or corrective dioptral values of patients' eye are measured by observing target images projected through the pupils and focused at the fundus of the patients' eye. More specifically, the present invention pertains to image rotating means for such eye refractometers.

Conventionally, eye refractometers comprise a target, a projecting optical system having a projection optical axis for projecting the target through a pupil of patient's eye, an observing optical system for observing an image of the target as produced on retina of the patient's eye, means for moving the target along the optical axis of the projecting optical system to focus the target image at the retina of the eye so that the refractive power of the patient's eye is determined in terms of corrective dioptral values in accordance with the position of the target. Further, in order for measurement of astigmatic axes, it is also required to provide means for rotating the projected target image. For the purpose, eye refractometers usually include an image rotator comprised of a planar mirror and a prism which are assembled together to rotate as a unit. Alternatively, the target may be rotated.

In operation of the conventional eye refractometers, it is required at first to rotate the projected target image to determine one of the astigmatic axes and then to move the target along the optical axes to measure the refractive power at the specific astimatic axis. Then, the target image is again rotated to determine the other astigmatic axis and the target is moved along the optical axis to measure the refractive power at the second astigmatic axis. Thus, in case of inspection of astigmatism, the measurements have to be carried out twice and there is unavoidable time difference between the first and second measurements. Since there may be self-adjustments by the patient, there may possibly be produced a difference in refractive powers between the respective measurements to thereby cause an error in measurements.

It is therefore an object of the present invention to provide eye refractometers which are simple in operation and have less possibility of producing measuring errors.

According to the present invention, the above and other objects can be accomplished by an eye refractometer comprising a target projecting optical system including a target and an optical axis for projecting the target to produce a target image on a patient's eye, an observing optical system for observing the target image on the patient's eye, means for rotating the target image, said image rotating means including first means for rotating the target image steplessly and second means for rotating the target image for 90° from any desired position. The rotating means may be comprised of an image rotating device provided along the optical axis of the target projecting optical system, a first member engaged with said image rotating device for producing a rotation of the image, a second member engaged with said first member so that the first member can be actuated for rotation without producing a rotation of the second member but an actuation of the second member produces rotation of the first and second members as a unit, means for stopping relative rotation between the first and second members after a relative rotation corresponding to a rotation of the target image of 90°.

According to the present invention, measurements are carried out by rotating the target image through the first means of the image rotating means to determine one of the astigmatic axes and measuring the refractive power at the specific astigmatic axis. Then, the target image is rotated for 90° by means of the second means to measure the refractive power at the other astigmatic axis. Since most of astigmatic eyes are of regular astigmatism in which the astigmatic eyes are perpendicular to each other, the above procedures are sufficient to accomplish the measurements substantially satisfactorily. The mechanism for effecting a 90° rotation can be embodied either by mechanical or electrical means. The present invention is advantageous in that the procedure for locating the second astigmatic axis is simplified so that the time between the first and second measurements is substantially shortened to thereby eliminate or decrease the possibility of errors.

The above and other objects and features of the present invention will become apparent from the following descriptions of a preferred embodiment taking reference to the accompanying drawings, in which.

Figure 1:
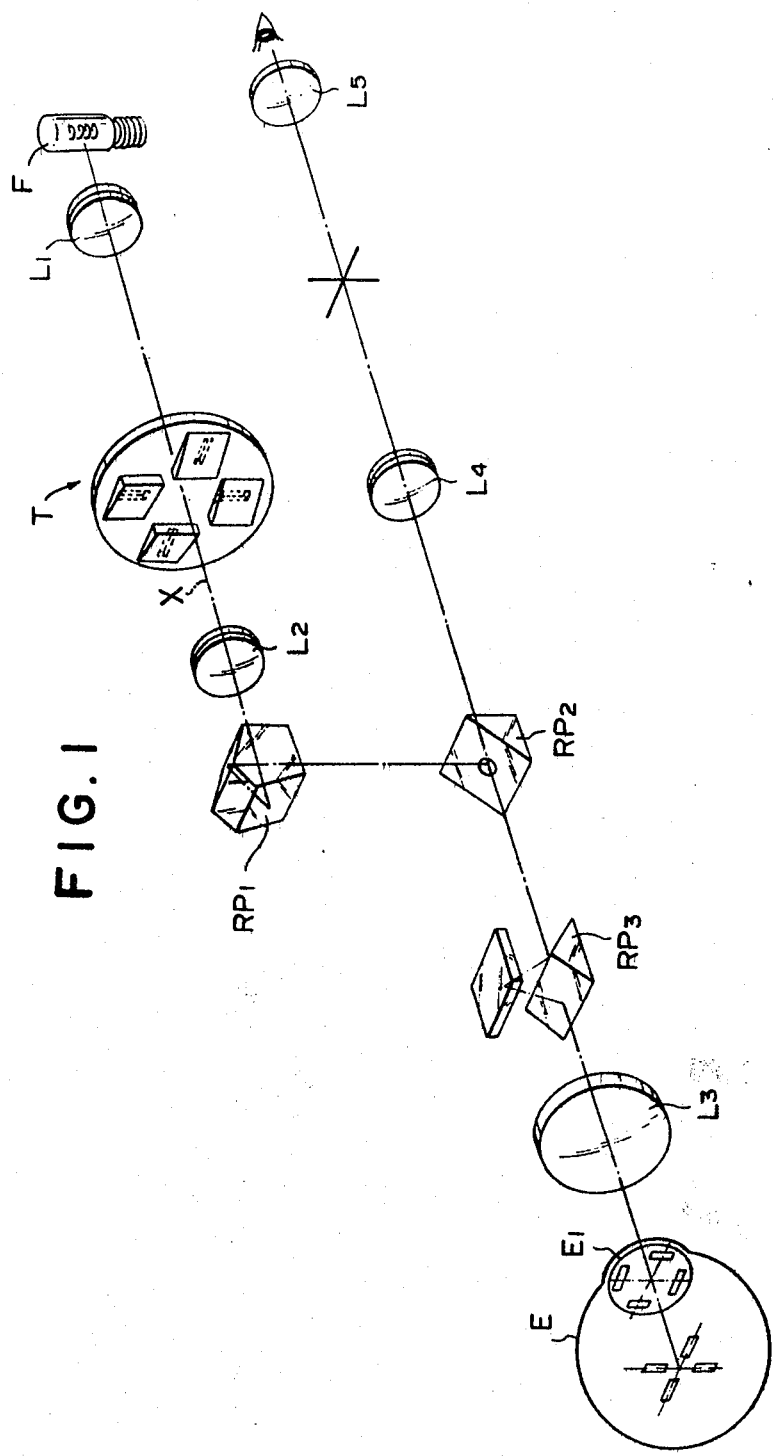
FIG. 1 is a perspective view showing an optical system of an eye refractometer in which the present invention can be applied.

Referring to the drawings, particularly to FIG. 1, the optical system of the eye refractometer shown therein comprises a projecting optical system and an observing optical system. The projecting optical system includes a light source F, a condenser lens $L_1$, a projecting lens $L_2$, a pentagonal prism $RP_1$, an apertured prism $RP_2$, an image rotator $RP_3$ comprised of a planar mirror and a prism and an objective lens $L_3$ which is adapted to be placed against the pupil $E_1$ of patient's eye E. The pentagonal prism $RP_1$ functions to reflect the light from the lens $L_2$ downwardly while the prism $RP_2$ functions to reflect the light from the prism $RP_1$ forwardly. Between the lenses $L_1$ and $L_2$, there is disposed a target T of a conventional type for a movement along an optical axis X. The observing optical system comprises lenses $L_4$ and $L_5$ for observing the image of the target as produced at the retina of the patient's eye E through the objective lens $L_3$ and the aperture in the prism $RP_2$.

Figure 2:
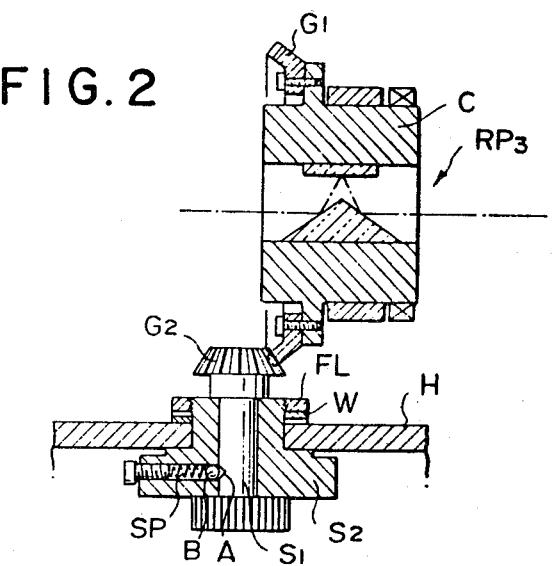
FIG. 2 is a sectional view of an image rotating mechanism in accordance with one embodiment of the present invention; and, FIG. 3 is a sectional view showing another embodiment of the present invention.

Referring to FIG. 2, there is shown an example of the mechanism for rotating the image rotation $RP_3$. The image rotator $RP_3$ has a case C which is attached with a bevel gear G1 meshing with a bevel gear G2 which is provided at one end of a first actuating shaft $S_1$. The first actuating shaft $S_1$ is passed through a second actuating shaft $S_2$ which is rotatably supported by a housing H of the instrument. The shaft $S_1$ is formed with recesses A which are adapted to receive a ball B retained in a bore of the shaft $S_2$. As shown, the ball B is biased toward the recess A by means of a spring SP.

The second shaft $S_2$ is provided with a flange FL and a corrugated washer W is disposed between the housing H and the flange FL. The recesses A are located in circumferentially spaced positions of which spacings are such that, when the first shaft $S_1$ is rotated by an angle corresponding to the spacing, a 45° rotation is produced in the image rotator $RP_3$ so that the projected target image is rotated by 90°. In the illustrated structure, an actuation of the second shaft $S_2$ produces a simultaneous rotation of the first shaft $S_1$ to thereby rotate the image rotator $RP_3$. The projected target image is therefore rotated until the orientation of the target is aligned with the direction of the astigmatic axis.

After the orientation of the target image has been aligned with one of the astigmatic axes, the target T is moved along the optical axis X until the target image is focused at the retina of the patient's eye. Thus, the refractive power is determined from the position of the target T. Then, the first actuating shaft $S_1$ is actuated to have the target image aligned with the second astigmatic axis. Since the second shaft $S_2$ is restrained from rotation by means of the washer W, the shaft $S_2$ is maintained stationary and only the shaft $S_1$ is rotated in this instance. The rotation of the first shaft $S_1$ is initiated by forcing the ball B out of one of the recesses A against the action of the spring SP and the rotation is stopped when the next one of the recesses A is aligned with the ball B. At this position, the projected target image has been rotated by 90° and the target T is then moved along the optical axis X to measure the refractive power of the patient's eye at this astigmatic axis.

Figure 3:
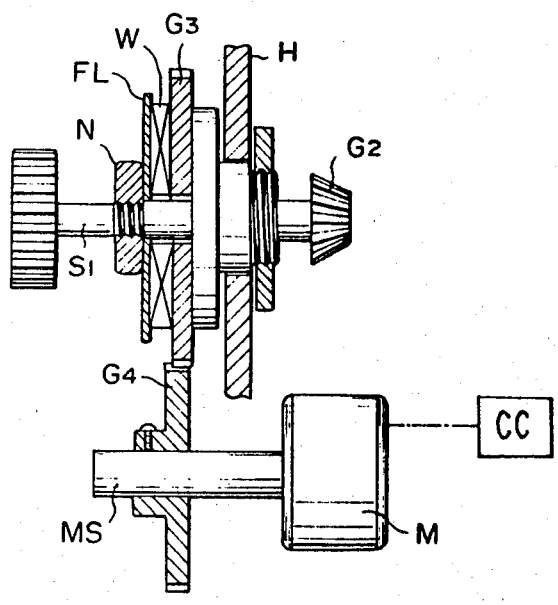

Referring now to FIG. 3 which shows another embodiment of the present invention, the mechanism includes a first actuating shaft $S_1$ which is rotatably supported on the housing H and has a bevel gear G2 meshing as in the previous embodiment with a bevel gear provided on a case of the image rotator. The shaft $S_1$ has a flange FL which is secured thereto and in contact with a corrugated spring W interposed between the flange FL and a gear G3. A pulse motor M is provided and has an output shaft MS which is provided with a gear G4. The gear G4 on the motor shaft MS is in meshing engagement with the gear G3. The pulse motor M is associated with an appropriate control circuit CC so that it rotates when actuated by an angle corresponding to a 90° rotation of the target image. The shaft $S_1$ is provided with a nut N which is adapted to adjust the contact pressure between the flange FL and the gear G3.

In this embodiment, an actuation of the shaft $S_1$ produces a stepless rotation of the image rotator and the actuation is continued until one of the astigmatic axes is located. Then, the target T is moved along the optical axis to focus the target image at the retina of the patient's eye. At this position, the refractive power of the patient's eye is read in terms of, for example, a corrective dioptral value. The pulse motor M is then actuated to rotate the target image by 90° to located the other astigmatic axis. Thereafter, the target T is again moved to focus the target image at the retina of the patient's eye so that the refractive power at this second astigmatic axis is measured. The pulse motor may be substituted by another type of D.C. or A.C. motor which may be controlled by means of limit switches.

The invention has thus been shown and described with reference to specific embodiments, however, it should be noted that the invention is in no way limited to the details of the illustrated arrangement but changes and modifications may be made without departing from the scope of the appended claims.

We claim:

1. An eye refractometer comprising a target projecting optical system including a target and an optical axis for projecting the target to produce a target image on a patient's eye, an observing optical system for observing the target image on the patient's eye, and means for rotating the target image, said image rotating means comprising an image rotating device provided along the optical axis of the target projecting optical system, a first member engaged with said image rotating device for producing a rotation of the image, a second member engaged with said first member so that the first member can be actuated for rotation without producing a rotation of the second member but an actuation of the second member produces a rotation of the first and second members as a unit, and means for stopping relative rotation between the first and second members after a relative rotation corresponding to a rotation of the target image of substantially 90°.

2. Eye refractometer in accordance with claim 1 in which said stopping means comprises recess means formed in one of the first and second members and a stopping element adapted to be engaged with said recess means.

3. An eye refractometer comprising a target projecting optical system includiing a target and an optical axis for projecting the target to produce a target image on a patient's eye, an observing optical system for observing the target image on the patient's eye, and means for rotating the target image, said image rotating means comprising an image rotating device provided along the optical axis of the target projecting optical system, a manual actuating member engaged with said image rotating device for producing a rotation of the image, a pulse motor engaged with said image rotating device for producing rotation of the image, and means for controlling said pulse motor so that the image is rotated by substantially 90°.

* * * * *